United States Patent [19]
Polaschegg

[11] Patent Number: 5,304,349
[45] Date of Patent: Apr. 19, 1994

[54] APPARATUS FOR DISINFECTION OF HEMODIALYSIS DEVICES WITH A POWDERED CONCENTRATE

[75] Inventor: Hans-Dietrich Polaschegg, Oberursel, Fed. Rep. of Germany

[73] Assignee: Fresenius AG, Bad Homburg v.d.H., Fed. Rep. of Germany

[21] Appl. No.: 966,098

[22] Filed: Oct. 22, 1992

[30] Foreign Application Priority Data

Nov. 20, 1991 [DE] Fed. Rep. of Germany ....... 4138140

[51] Int. Cl.⁵ .................................................. B01L 11/00
[52] U.S. Cl. ..................................... 422/101; 422/99; 422/102; 422/103; 422/105
[58] Field of Search ............... 422/292, 302, 103, 105, 422/102, 101, 99, 116

[56] References Cited

U.S. PATENT DOCUMENTS

| | | | |
|---|---|---|---|
| 4,508,622 | 4/1985 | Polaschegg et al. | 210/321.65 |
| 4,683,053 | 7/1987 | Polaschegg | 210/321.6 |
| 4,707,335 | 11/1987 | Fentress et al. | 210/321.71 |
| 4,789,467 | 12/1988 | Lindsay et al. | 210/321.69 |
| 4,895,657 | 1/1990 | Polaschegg | 210/321.71 |
| 4,923,598 | 5/1990 | Schai | 210/321.65 |

Primary Examiner—James C. Housel
Assistant Examiner—Lien Tran
Attorney, Agent, or Firm—Jack Schuman

[57] ABSTRACT

A hemodialysis device (10) which features an improved disinfection apparatus. Before disinfection begins, a container (30) of disinfectant (36) is interposed into the dialysis fluid circulation system in place of the dialyzer. The dialysis fluid circulation system is shunted, and the disinfecting solution which is present in this closed circulation system is flushed out of the container (30) and through the entire path of the dialysis fluid, in order to achieve a complete cleaning of the hemodialysis device (10). It is possible to use solid, soluble disinfectant (36) as well as liquid disinfectant.

20 Claims, 1 Drawing Sheet

APPARATUS FOR DISINFECTION OF HEMODIALYSIS DEVICES WITH A POWDERED CONCENTRATE

BACKGROUND OF THE INVENTION

(1) Field of the Invention

The invention pertains to disinfection apparatus for use with hemodialysis apparatus.

(2) Description of the Prior Art

One of the features of blood dialysis apparatuses—so-called hemodialysis devices—is a circulation system for dialysis fluid. This circulation system features a water supply and a dialyzer. The water supply and dialyzer are connected to one another by an initial fluid line. A second fluid line leads from the dialyzer to the discharge. The first and second fluid lines each feature a connector which connects the respective line to the dialyzer. While the dialysis fluid circulation system is being disinfected, a disinfecting apparatus is interposed into this circulation system, and the two fluid lines are connected in a bypassing manner by a shunt piece between their respective connectors.

The disinfection of hemodialysis devices is an essential cleaning step between successive dialysis processes. The goal of this disinfection is the complete cleaning and sterilization of all surfaces and devices which come into contact with the dialysis fluid and/or its concentrates or thinning fluids. Inadequate disinfection of the dialysis fluid circulation system can lead to considerable damage to the health of the patient being treated. However, the only parts of the hemodialysis device which undergo disinfection are those which can be considered part of the dialysis fluid circulation system. The reason for this is that all parts of the blood circulation system are removed and replaced by new, sterile parts after each dialysis process.

In a familiar method for cleaning hemodialysis devices, the dialysis concentrate is replaced by a disinfectant concentrate (typically from a 10-liter canister), which is pumped through the hemodialysis device. In this method, the two fluid lines (i.e., water supply line and dialysis fluid discharge line) are not shunted together. When disinfection has been completed, the disinfecting fluid remains inside the device. Before beginning the next dialysis process, the dialysis device is flushed with water. This process requires the use of a great quantity of the disinfectant. It accomplishes the cleaning of only that portion of the dialysis apparatus which is located downstream from the point at which the disinfectant is added. The applicant's hemodialysis devices A2008C-E are typical embodiments of these devices.

Improved embodiments—as represented, for example, in DE 3 447 989 and DE 3 941 103—recirculate the disinfecting solution after interposing a shunt connection between the first and second fluid lines. For one thing, this results in the complete cleaning of the dialysis fluid circulation system. It also reduces the consumption of disinfectants.

Liquid cleaning agents (e.g., formaldehyde, peracetic acid, sodium hypochlorite, or similar chemicals) are ordinarily used as disinfectants. These cleaning agents are aggressive, environmentally unsound, unhealthy, and even somewhat poisonous. It is especially necessary to exercise great caution when using mixtures of the above-mentioned cleaning agents, since an explosion or a release of elemental chlorine can occur. It has only recently been discovered that citric acid functions as a disinfectant at high temperatures. Concentrated citric acid is also aggressive and can cause dangerous reactions when mixed with other chemicals.

Aside from the high cost of transporting the disinfectant (which consists mainly of water), it is necessary to exercise great caution when replacing the concentrates for the dialysis fluid and disinfectant. To this end, special precautions have been taken to prevent the different liquids from being misrouted, i.e, to prevent these concentrates from being accidentally exchanged with one another. Examples of such precautions include special provisions for connecting the different canisters to the hemodialysis device and separate controls for the fluid lines.

There is therefore an urgent need for a disinfecting apparatus which reduces the danger of accidental exchange described above, while ensuring a safe, complete disinfection of the hemodialysis device.

SUMMARY OF THE INVENTION

This problem is solved by providing the disinfecting device with a container which features two adapters for the purpose of attachment to the first and second connectors. This container contains a predetermined dose of a disinfectant.

The container of the disinfecting apparatus can take the form of an apparatus which is rigidly attached to the machine and features a stopper, or it can be a disposable or recyclable container which is externally refillable.

In one advantageous embodiment of the invention, the adapters are designed in accordance with DIN (German Industrial Standard) 58 352. This prevents the connections from being accidentally exchanged and makes the adapters universally applicable.

It is also advantageous to provide the container with a closable fill opening which is suitable for receiving a dose of the disinfectant when refilling.

In one preferred embodiment of the invented apparatus, a filter is provided inside the disinfectant container, in the vicinity of the discharge adapter. The pores or grid openings of this filter are smaller than the grain size of the disinfectant powder. Portions of the disinfectant powder which have not yet dissolved are thus retained.

An upwards flow through the container of the disinfecting apparatus and a tangential inflow of water into the container prove to be especially favorable to the distribution and dissolution (where applicable) of the disinfectant.

When a liquid disinfectant is used, it is advantageous to provide a non-return valve in the refillable container, in the region of the discharge adapter. The non-return valve can be opened by the pressure of the onrushing water. It is located in a lower position during operation.

In an especially preferred embodiment of this invention, a powdered disinfectant (e.g., crystalline or granulated citric acid) is used for disinfection. A special advantage of using solid disinfectants is that it prevents the accidental exchange of disinfecting fluid and dialysis fluid, which has occasionally occurred in the past. This makes the disinfection of hemodialysis devices considerably safer. The citric acid is provided in a suitable dose—for example, in a quantity of 5-30 grams for each liter of the volume to be disinfected. The container is designed to hold such a quantity. When the container is full, an unhindered flow can occur through the container. This ensures that the citric acid solution is recirculated within the hemodialysis device in a sufficiently high concentration. It also ensures that disinfection will occur safely and completely.

In another embodiment of the invention, it is also possible for the closable container of the disinfection apparatus to be filled with a liquid cleaning agent (e.g., solutions of peracetic acid, formaldehyde, or sodium hypochlorite). The use of individual packages of concentrate solutions also offers the considerable advantage of allowing the refill packages to be unmistakably distinguished from the containers of dialysis fluid, so that accidental exchanges can be prevented more effectively than in the past. Another advantage of using cleaning agent concentrates is a reduction in the transport volume of the cleaning agent, which in turn results in cost savings.

The dialysis fluid tubes are connected to the dialyzer during dialysis. After dialysis is concluded, the dialyzer is removed and the respective connectors of the first and second fluid lines are connected to the container of the disinfecting device. It is advantageous for a holder and sensor to be mounted on the hemodialysis device. The sensor allows the positioning of the container to be determined with certainty, so that the presence and appropriate arrangement of the disinfecting device can be monitored simply and with certainty at all times.

In order to further ensure the certainty of monitoring the disinfecting device, one preferred embodiment of the invention provides additional sensors in the connectors which connect the refillable container of the disinfecting apparatus to the first and second fluid lines. These sensors make it possible to check for secure connections between these connectors and the container. The sensors do not allow the disinfecting operation to begin until this connection exists.

In order to allow a clear distinction between a simple rinsing of the hemodialysis device and a complete disinfection process, the container of the disinfecting apparatus can be controlled by means of a bypass valve. This bypass valve can be either electrically controllable or mechanically operable and electrically readable.

In one advantageous embodiment of this invention, the supply line, discharge line and/or dialysis fluid supply are connected by a recirculation line. The apparatus features a closing device for the purpose of creating the recirculation system. With the recirculation system closed in this manner, a complete cleaning of all parts and surfaces of the dialysis fluid circulation system is ensured.

DESCRIPTION OF THE DRAWING

A preferred embodiment of the invention is represented in FIGS. 1 and 2 below.

DESCRIPTION OF THE PREFERRED EMBODIMENTS

Figures 1, 2:
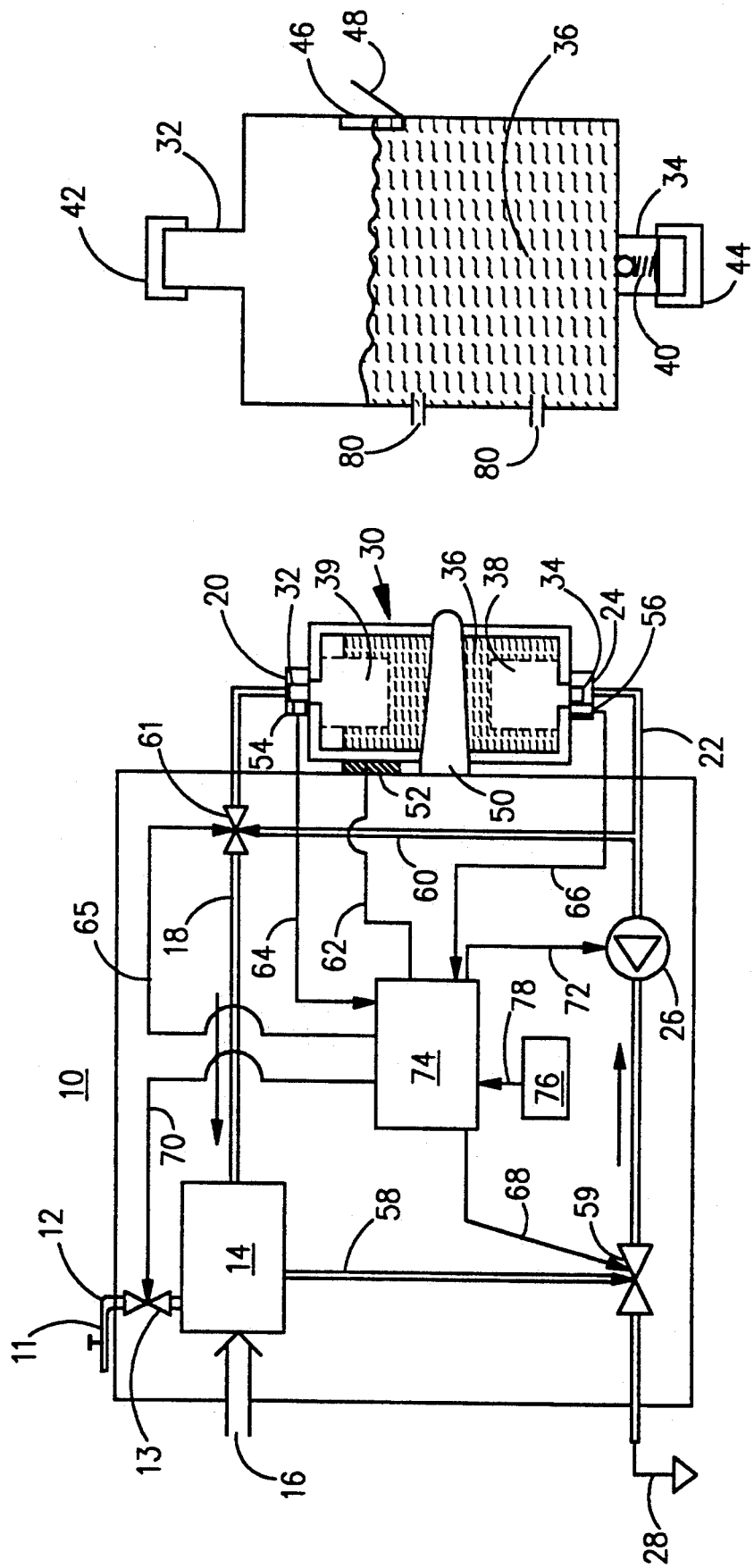
FIG. 1 represents a diagram of a hemodialysis device during the disinfecting process, in a sectional view.
FIG. 2 represents a section through a container of the disinfecting apparatus.

The hemodialysis device 10 represented in FIG. 1 features a water supply 11, which empties into a mixing container 14 (dialysis fluid supply) via a line 12, in which a valve 13 is inserted. The mixing container is in turn connected to a supply 16 of an electrolyte concentrate. An initial fluid line 18 exits the mixing container 14. The end of this initial fluid line protrudes from the hemodialysis device 10 and features an initial connector 20. This initial connector 20 is ordinarily connected to a dialyzer (not shown) during dialysis.

A second fluid line 22 leads back into the hemodialysis device 10. This second fluid line features a second connector 24 on the end which is located outside the hemodialysis device 10. This second connector is connected to the discharge of the dialyzer (not shown) during dialysis.

A pump 26 is interposed in the second line 22 inside the hemodialysis device 10. The other end of the second line 22 is ultimately connected with the discharge 28. This type of dialysis device represents the state of the art and is therefore not the object of this invention.

The hemodialysis device 10 is represented in FIG. 1 as it functions during the disinfection phase. For this purpose, a disinfectant container 30 is provided between the two connectors 20 and 24. It is advantageous for this container to display a hollow cylindrical form. This disinfectant container 30 features a supply adapter 32 and 34 at each of its two ends. These two adapters 32 and 34 can be connected in a form-fitting manner to the two connectors 20 and 24. It is advantageous for these adapters to display a form identical to that of the adapters of the dialyzer (not shown), since the latter are subject to international standards of uniformity. In accordance with this embodiment, these adapters take the form of the connection specified by DIN (German Industrial Standard) 58 352. Connectors 20 and 24 are also designed in accordance with this standard. According to one preferred embodiment, at least one of the adapters 32 or 34—through which the fluid flows into the container 30—is arranged tangentially to the longitudinal axis of the hollow cylindrical container 30. This optimizes the flow of fluid into, and out of, the container 30.

The disinfectant container 30 is filled with a disinfectant 36 which can display a granular (i.e., powdered) structure, as represented in FIG. 1.

A grid-shaped cylindrical filter 38 is provided inside the disinfectant container 30, in the region of the discharge adapter 34. This filter is completely enclosed and displays an average mesh opening size which is smaller than the disinfectant particles. The purpose of this filter 38 is to retain undissolved disinfectant within the disinfectant container 30. In the embodiment represented in FIG. 2, a liquid disinfectant concentrate 36 is provided inside the disinfectant container 30. The container 30 represented in FIG. 2 is shown as positioned for use; in other words, the discharge adapter 34 is located on the bottom. In order to prevent the liquid disinfectant 36 from flowing out while the connections are being made, a non-return valve 40 is provided in the discharge adapter 34. This non-return valve can be opened by the pressure of the onrushing mixture of water and disinfectant.

Before being used, the disinfectant container 30 features caps 42 and 44 at both of its connections 32 and 34. These caps close off the two connections 32 and 34 and can be opened when necessary.

A fill opening 46 can also be provided in the container 30. This opening is closed off by a cover 48.

A holder 50 for the disinfectant container 30 is mounted on the hemodialysis device 10. In the example represented here, this holder takes the form of two clamping jaws 50 which can be folded open. An initial sensor 52 is also mounted on the hemodialysis device 10 in the vicinity of this holder 50. This sensor is activated by the container 30 when the container is inserted into the holder 50. The sensor displays a predetermined positioning of the container 30. This sensor 52 is activated by the container 30, but not by the dialyzer, in the event that the dialyzer is inserted into the holder 50. This ensures that a container 30 is inserted and mounted on the dialysis device 10 in a predetermined position.

Connectors 20 and 24 can also be equipped with contact sensors 54 and 56, which are connected to the hemodialysis device 10 via a connecting line, as shown symbolically in FIG. 1. With these contact sensors 54 and 56, it is possible to monitor the connection between the connectors 20 and 24 and the connections 32 and 34.

In another embodiment, the second line 22 is connected to the mixing container 14 via a bypass line 58. Here the point of connection between the bypass line 58 and the line 22 features a valve arrangement 59. This valve arrangement provides the options of connecting the second line 22 to the discharge 28 or—in the recirculating operation—to the mixing container 14 via the bypass line 58.

The supply line 16 and discharge line 22 are connected to the conventional bypass line 60, and a bypass valve 61 is provided at the point at which the two lines are connected. The sensors 52-56, valve arrangement 59, fresh water valve 13 and dialysis fluid pump 26 are connected to a control unit 74 via lines 62-72. The control unit is connected to an input unit 76 via line 78.

As represented by the indicated arrows, the control unit 74 for performing disinfection can not be activated until the sensors 52-56 have sent the connection signal to the control unit 74 via lines 62-66 and the input unit 76 has been activated by the operator.

The hemodialysis device 10 is operated in the following manner, in order to begin disinfection:

The dialyzer is first detached from the connectors 20 and 24. The container 30, which has been filled with fresh disinfectant, is then connected to the two connectors 20 and 24 by its adapters 32 and 34. The contact sensors 54 and 56 ensure a form-fitting connection and notify the control unit 74 of this connection.

The container 30 is then moved into a predetermined position in relation to the hemodialysis device 10. This is accomplished by inserting the container into the holder 50, where it activates the sensor 52. This sensor notifies the control unit 74—via the connecting line 62—of the appropriate predetermined position. The disinfection program can now be started by activating the input unit 76. In addition, the water supply 11 is activated by opening the valve 13, and the valve arrangement 59 is put into the recirculating operation. In accordance with an initial predetermined program sequence, which is stored in the control unit 74, the water is then led through the entire arrangement of lines 18, 22, 58, 14. This continues until the entire quantity of disinfectant is uniformly distributed within this system of lines. The disinfecting solution is then allowed to act upon the hemodialysis device 10 long enough to ensure that the entire dialysis system has been disinfected. A fresh water rinse is then performed by connecting the valve arrangement 59 alternately with the discharge 28 and the recirculation line 58 for rinsing. On the other hand, it is also possible to leave the device 10 filled with the disinfecting solution and rinse it shortly before using it again. Finally, it can also be advantageous to activate the bypass valve 61 via the connecting line 65 when it is intended that the water or disinfecting solution shall flow through the entire apparatus except the container 30. The hemodialysis device 10—which is now sterile and filled with fresh water—can then be used for another dialysis process. To this end, the disinfectant container 30 is detached from the connectors 20 and 24. These connectors are then connected to a sterile, unused dialyzer.

In accordance with another method—the parameters of which are also stored in the control unit 74—the flow through the container occurs in an upwards direction when the container is positioned for operation. To this end, the pump 26 is switched by the control unit to pump in the opposite direction. The advantage of this type of method is that the powder 36 in the container 30 is swirled upwards, so that the discharge adapter 34 does not become clogged. On the other hand, this type of operation can also be achieved by mounting the end of the supply line 18 with the connector 20 at the bottom of the container 30 when positioned for use, while the discharge line 22 is attached at the top of the container 30. In this case, it is not necessary to reverse the output direction of the pump 16. When the flow occurs upwards within the container 30, it is also advantageous to arrange a filter 39 at the upper adapter 32. (This filter may be similar to the other filter 38.) As a result, the discharge of undissolved powder is prevented.

For example, if solid citric acid granulate is used for disinfection, between 10 and 60 grams should be sufficient to fill the container 30 while achieving a disinfectant concentration of 0.5-3.0%. (This number of grams corresponds to a required volume of less than 100 milliliters. It also assumes that the filling volume of the hemodialysis device is 2 liters, and that the density of the granulated citric acid is approximately 1.) This amount of disinfectant can be put into the empty container 30 through the fill opening 46. The container can then again be used for disinfection. In order to ensure that the container is filled with the required amount of disinfectant, the container 30 can feature markings 80 on its outside. These markings can be used to determine the correct fill level and the quantity of disinfectant which has actually been added, provided that a transparent plastic material (e.g., polycarbonate) is used.

I claim:

1. Apparatus for dialysis (10) comprising water supply (11), dialysis fluid supply container (14), supply line (18) having a first end and a second end, the first end of said supply line (18) being connected to said dialysis fluid supply container (14), a first connector (20) mounted to the second end of said supply line (18), said second end of said supply line (18) being selectively connected to a dialyzer by means of said first connector (20), discharge line (22) having a first end and a second end, a second connector (24) mounted to the first end of said discharge line (22), said first end of said discharge line (22) being selectively connected to said dialyzer by means of said second connector (24), said second end of said discharge line (22) leading to discharge line (28), and disinfection apparatus connected during disinfection cycle both to said dialysis fluid supply container (14) through said supply line (18) and to discharge line (22), said discharge line (22) can be selectively connected to supply container (14) through a recirculating line (58) to permit recirculating operation, wherein during said disinfection cycle a bypass valve (61) in said supply line (18) can be selectively activated through a connecting line (65) to allow for disinfection of the entire dialysis apparatus characterized in that:

(a) said disinfection apparatus comprises container (30) having a first end and a second end to hold a predetermined quantity of disinfectant (36), (b) a third connector (32) mounted to said container (30) at the first end thereof and connected in fluid-tight relationship to said first connector (20) at the second end of said supply line (18), (c) a fourth connector (34) mounted to said container (30) at the second end thereof and connected in fluid-tight relationship to said second connector (24) at the first end of said discharge line (22).

2. Apparatus as in claim 1, further characterized in that said third connector (32) and fourth connector (34) are DIN (German Industrial Standard) type 58 352 connectors.

3. Apparatus as in claim 1, further characterized in that said container (30) has fill opening (46) which can be closed by cover (48) and which permits refilling with a dose of disinfectant (36).

4. Apparatus as in claim 1, further characterized in that filter (38) is provided in said container (30) adjacent said fourth connector 34, and said container (30) holds disinfectant (36) in the form of a powder.

5. Apparatus as in claim 1, further characterized in that:

(a) valve (40) is provided in the fluid circuit between said container (30) and said discharge line (22) adjacent said fourth connector (34) and is under fluid pressure in said fluid circuit to place the interior of said container (30) in communicating relationship with said discharge line, (b) said container (30) holds said disinfectant (36) in the form of a liquid.

6. Apparatus as in claim 1, further characterized in that holder (50) and sensor (52) are mounted on a side of apparatus (10), said sensor (52) determines the positioning of said container (30) within said holder (50).

7. Apparatus as in claim 1, further characterized in that a first contact sensor (54) is mounted to said first connector (20), and a second contact sensor (56) is mounted to said second connector (24), said first contact sensor (54) monitoring the connection between said first connector (20) and said third connector (32) to insure a fluid-tight connection therebetween, said second contact sensor (56) monitoring the connection between said second connector (24) and said fourth connector (34) to insure a fluid-tight connection therebetween.

8. Apparatus as in claim 1, further characterized in that said supply line (18), said discharge line (22) and said dialysis fluid supply container (14) are connected to one another by said recirculation line (58), and valve means (59) is interposed in the fluid circuit between said recirculation line (58) and said discharge line (22) to permit fluid flow from said discharge line (22) to discharge line (28) or selectively to permit fluid flow from discharge line (22) to said recirculation line (58).

9. Apparatus as in claim 1, further characterized in that said disinfectant (36) is citric acid and is present in said container (30) in a concentration of 5-30 grams per liter of the volume of apparatus (10) to be disinfected.

10. Apparatus as in claim 1, further characterized in that said disinfectant (36) in said container (30) is selected from the group consisting of solutions of peracetic acid, formaldehyde and sodium hypochlorite.

11. Apparatus as in claim 1, further characterized in that flow of said disinfectant (36) through said container (30) is from top to bottom thereof.

12. Apparatus as in claim 11, further characterized in that the flow of said disinfectant (36) through said container (30) is continuous.

13. Apparatus as in claim 11, further characterized in that flow of said disinfectant (36) through said container (30) is from bottom to top thereof.

14. Apparatus as in claim 13, further characterized in that the flow of said disinfectant (36) through said container (30) is continuous.

15. A container (30) adapted to contain disinfectant (36) for disinfecting a hemodialysis apparatus (10) during a disinfecting cycle operation thereof, said hemodialysis apparatus having a first connector (20), a second connector (24), a supply line (18), a discharge line (22), a recirculating line (58) and a fluid supply container (14), said container comprising:

(a) storage volume therein adequate to contain a predetermined quantity of said disinfectant (36) sufficient for disinfecting said hemodialysis apparatus (10) during one disinfecting cycle operation thereof, (b) a first end and a second end on said container, (c) a third connector (32) mounted to said container (30) at the first end thereof and to be connected in fluid-tight relationship to said first connector (20) prior to commencement of said disinfecting cycle of said hemodialysis apparatus (10) and to be disconnected from said first connector (20) after completion of said disinfecting cycle, (d) a fourth connector (34) mounted to said container (30) at the second end thereof and be connected in fluid-tight relationship to said second connector (24) prior to commencement of said disinfecting cycle of said hemodialysis apparatus (10) and to be disconnected from said second connector (24) after completion of said disinfecting cycle, (e) whereby, in said disinfecting cycle, said disinfectant (36) flows through said container (30) from said first end of said container (30) to said second end thereof and is circulated through said supply line (18), said discharge line (22), said recirculating line (58) and said fluid supply container (14) of said hemodialysis apparatus.

16. Container (30) as in claim 15, wherein:

(f) said first end of said container (30) is at the top thereof, (g) said second end of said container (30) is at the bottom thereof, (h) said disinfectant (36) flows through said container (30) from said first end of said container (30) to said second end thereof.

17. Container (30) as in claim 15, wherein:

(f) said first end of said container (30) is at the top thereof, (g) said second end of said container (30) is at the bottom thereof, (h) said disinfectant (36) flows through said container (30) from said first end of said container (30) to said second end thereof.

18. Container (30) as in claim 15, further comprising:

(f) fill opening (46) for introducing solid or liquid disinfectant (36) into said container (30), (g) cover (48) removably positioned over said fill opening (46).

19. Container (30) as in claim 15, further comprising:

(f) filter (38) mounted within said container (30) and interposed between the first and second ends thereof.

20. Container as in claim 15, further comprising:

(f) non-return valve (40) mounted adjacent said fourth connector (34) to be opened under fluid pressure to place the interior of said container (30) in communicating relationship with said fourth connector (34).

* * * * *

UNITED STATES PATENT AND TRADEMARK OFFICE
CERTIFICATE OF CORRECTION

PATENT NO. : 5,304,349

DATED : April 19, 1994

INVENTOR(S) : Hans-Dietrich Polaschegg

It is certified that error appears in the above-identified patent and that said Letters Patent is hereby corrected as shown below:

Col.7
Claim 5, line 5, after "is" insert --opened--.
Col. 8
Claim 13, line 1, after "claim" delete "11" and substitute
    therefor --1--.
Claim 17, line 7, before "end" delete "first" and
    substitute therefor --second--; line 8, before
    "end" delete "second" and substitute therefor "first".

Signed and Sealed this

Twenty-sixth Day of July, 1994

Attest:

BRUCE LEHMAN

Attesting Officer

Commissioner of Patents and Trademarks